United States Patent [19]

Kaufman et al.

[11] Patent Number: 4,763,651
[45] Date of Patent: Aug. 16, 1988

[54] TREPHINE AND METHOD

[75] Inventors: Herbert E. Kaufman; Marguerite B. McDonald, both of New Orleans, La.

[73] Assignee: Allergan, Inc., Irvine, Calif.

[21] Appl. No.: 818,737

[22] Filed: Jan. 14, 1986

Related U.S. Application Data

[63] Continuation-in-part of Ser. No. 670,396, Nov. 8, 1984.

[51] Int. Cl.⁴ .............................................. A61B 17/32
[52] U.S. Cl. ..................................... 128/310; 128/305
[58] Field of Search ............... 128/92 R, 92 V, 305.1, 128/310, 317, 305, 304; 30/174, 300, 301, 310

[56] References Cited

U.S. PATENT DOCUMENTS

| | | | |
|---|---|---|---|
| 1,043,408 | 11/1912 | Vilbiss | 128/305.1 |
| 1,837,067 | 12/1931 | Reiter | 128/92 V |
| 2,249,906 | 7/1941 | Longoria | 128/305 |
| 2,473,968 | 6/1949 | Paton | 128/305 |
| 2,818,852 | 1/1958 | Kugler | 128/305 |
| 4,205,682 | 6/1980 | Crock et al. | 128/305 |
| 4,423,728 | 1/1984 | Lieberman | 128/310 |
| 4,429,696 | 2/1984 | Hanna | 128/310 |
| 4,526,171 | 7/1985 | Schachar | 128/305 |

FOREIGN PATENT DOCUMENTS

| | | | |
|---|---|---|---|
| 1185860 | 4/1985 | Canada | 128/317 |
| 2487667 | 2/1982 | France | 128/305.1 |
| 545342 | 2/1977 | U.S.S.R. | 128/305.1 |

Primary Examiner—Carl D. Friedman
Assistant Examiner—Michael Safavi
Attorney, Agent, or Firm—Gordon L. Peterson

[57] ABSTRACT

A trephine for cutting a groove in the cornea of an eye comprising a fixation member and a shaft having first and second blades mounted thereon. The fixation member includes a bearing, and the shaft is receivable within the bearing. The fixation member can be affixed to the eye, and the shaft, when received in the bearing, is rotatable in the bearing so that the blades can make cuts in the cornea. By making cuts in the cornea which intersect, a segment of the cornea can be removed to provide the groove.

18 Claims, 6 Drawing Sheets

TREPHINE AND METHOD

BACKGROUND OF THE INVENTION

This application is a continuation-in-part of application Ser. No. 670,396 filed on Nov. 8, 1984, and entitled Trephine and Method.

In the medical treatment of certain conditions of the eye, it is sometimes necessary or desirable to form a groove in the cornea. The groove may be formed near the outer perimeter of the cornea so that replacement corneal tissue can be tucked into the groove and sewed in place.

The groove, which may be annular, can be formed by making two intersecting cuts in the cornea. These cuts must be made very carefully to a shallow depth which may be, for example, about 0.2 to about 0.4 millimeters (mm). It is extremely difficult to carefully and accurately make shallow incisions on the corneal surface due to the non-rigid nature of the eye.

A trephine can be used to make an incision in the cornea. One prior art trephine includes a hollow cylinder having a cylindrical razor blade at one end for forming a generally vertical cut in the periphery of the cornea for 360 degrees. Scissors are then used to manually form an angle cut in the cornea which intersects the vertical cut, and the resulting segment can be removed from the cornea to provide a groove. Unfortunately, it is exceedingly difficult to accurately control the scissors-cutting operation, and it takes a relatively long time to complete the scissors cut.

Lieberman U.S. Pat. No. 4,423,728 discloses a trephine which can make both of the cuts in the cornea, thereby eliminating the need for a scissors cut. However, this trephine is very complex and provides for numerous adjustments of the blade which introduce a possibility of human error in the corneal-cutting procedure.

SUMMARY OF THE INVENTION

This invention provides a trephine of simple construction which eliminates many of the possibilities for human error in the corneal-cutting procedure. Some of the concepts of this invention can be embodied in a trephine which comprises a fixation member and first and second shafts, with each of the shafts having a blade mounted thereon. The fixation member must be fixable to the eye and support the shafts for rotation. For these purposes, it includes suitable means cooperable with the eye for fixing the fixation member to the eye and a bearing having a passage for receiving and mounting the shafts for rotation about a rotational axis.

In use, the first shaft is inserted into the bearing to a first axial position in which the associated blade is in contact with the cornea, and the shaft is then rotated to form a first cut in the cornea. The first shaft is then withdrawn, and the second shaft is inserted into the bearing to a second axial position and rotated to form a second cut which intersects the first cut. This provides a severed corneal segment which can be removed to provide a groove in the cornea.

Several factors combine to enable the trephine of this invention to accurately and rapidly provide the desired cut. For example, each of the blades is mounted on the associated shaft, with the cutting edge of the blade projecting a fixed distance beyond the end wall of the shaft. In use, the shaft can be axially advanced into the bearing until the end wall of the shaft engages the cornea. Therefore, the depth of cut is accurately related to the fixed distance that the blade projects beyond the end wall. This also reduces the likelihood of human error in establishing the depth of the cut. In addition, fixedly mounting the blade contributes to simplicity in the construction.

The fixation member also contributes to the accuracy of the results by being accurately fixable to the eye. Although various forms of fixation can be employed, complexity is reduced by eliminating the vacuum fixation techniques of the prior art in favor of teeth on the fixation member located to engage the sclera of the eye. The teeth can advantageously be provided on one or more legs coupled to the bearing and located radially outwardly of the bearing.

Rotation of the shafts in the bearing in a first direction tends to rotate the fixation member in that same direction. To more firmly fix the fixation member on the cornea and to enable it to strongly resist rotation of the fixation member in the first direction, at least one, and preferably all, of the teeth terminate in a distal end portion which extends generally in such first direction. Accordingly, any tendency of the fixation member to rotate in the first direction results in digging the distal end portions of the teeth farther into the cornea to resist rotation of the fixation member.

In one embodiment, the leg of the fixation member and the inner end of the bearing terminate in the same plane. However, it is preferred to have the leg project axially beyond the inner end of the bearing in the direction of the teeth to provide a space into which the cornea can bulge when the fixation member is placed against it. This construction is preferred because it facilitates the removal of an annular segment from the cornea to form the desired groove.

The features of this invention may be used to form one or more cuts in the cornea. If the cuts are to define a segment which can be removed from the cornea to form a groove, then the blades on the two shafts must be appropriately oriented relative to the associated shaft to perform this function. Alternatively, if the features of this invention are to be utilized to form, for example, only a single cut, then only a single shaft is needed, and the blade used for that cut must have an appropriate orientation to provide the desired cut.

Although the exposed portion of the blade can be constructed of different materials, one preferred material is a diamond. A diamond has the advantages of being sharp and difficult to dull. Another preferred material for the blade is a ruby. A ruby has the advantages of being of lower cost than a diamond blade and being easier to manufacture. A sapphire or other real or synthetic gem material may also be utilized.

To protect the blade from damage, the exposed portion of the blade preferably lies entirely within the perimeter of the peripheral wall of the shaft as viewed in a direction perpendicular to the end wall of the shaft. Also, the bearing only partially circumscribes the passage of the bearing at the outer end of the bearing to permit insertion of the shaft in the passage with reduced likelihood of damage to the blade.

The shaft and blade form a knife. The blade is preferably fixedly mounted on the shaft by a mounting body of plastic. The mounting body can advantageously be retained in a groove of the shaft which opens at the end wall of the shaft. In order for the blade to make the desired vertical cut in the cornea, the blade is preferably adjacent the peripheral wall of the shaft, and the projecting portion of the blade is inclined radially inwardly. Because of the non-rigid nature of the cornea, this radial inclination of the blade is necessary to get an essentially vertical cut.

Another feature of this invention is that both of the first and second blades can be mounted on a single shaft. This has the advantage of minimizing the likelihood of damage to the blades due to contact with the bearing during insertion of the shaft into the bearing in that only one insertion is necessary to accomplish the surgery. In addition, it enables both of the cuts to be formed with a single operation.

To accomplish this, the first and second blades have first and second orientations, respectively, with respect to the axis of the shaft, with such orientations being arranged so that the cuts formed by the blades tend to enable a segment to be severed from the cornea to form the groove. Viewed from a different perspective, the cutting edges of the blades are arranged so that the cuts formed thereby lengthen circumferentially as the shaft is rotated so as to tend to form a groove in the cornea. Preferably, the blades project from the end wall of the shaft in directions which are generally transverse to each other. The cutting edges are preferably spaced circumferentially.

To facilitate rotation of the shaft carrying the blades, the shaft has a driving portion which is of less cross-sectional area than a major region of the shaft located distally of the driving portion. To further facilitate use of the knife, the driving portion of the shaft preferably terminates in an enlargement having a concave surface. The surgeon may place the index finger of his nondominant hand in the concave surface to apply suitable downward cutting force to the shaft.

The invention, together with additional features and advantages thereof, may best be understood by reference to the following description taken in connection with the accompanying illustrative drawing.

BRIEF DESCRIPTION OF THE DRAWING

FIGS. 12 and 13 are isometric views illustrating a second embodiment of the invention. Specifically.

DESCRIPTION OF THE PREFERRED EMBODIMENT

Figure 1:
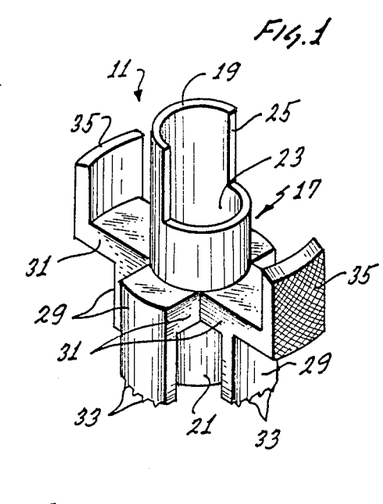
FIGS. 1-3 are isometric views illustrating, respectively, one form of fixation member and first and second knives constructed in accordance with the teachings of this invention.
Figure 2:
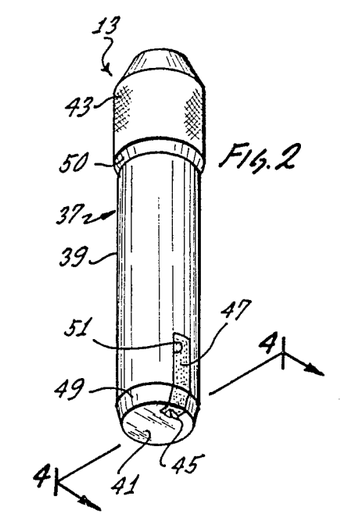
Figure 3:
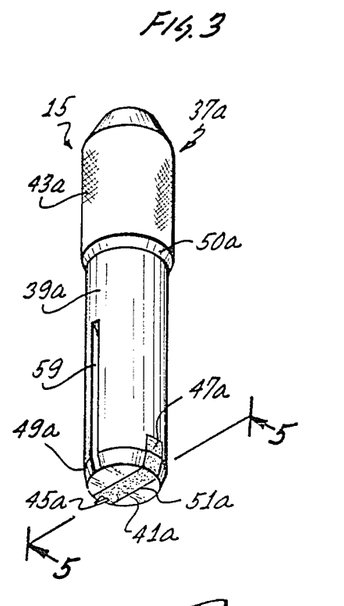

In the embodiment illustrated in FIGS. 1-11, the trephine includes a fixation member 11 (FIGS. 1 and 7) and one or more knives 13 and 15 (FIGS. 2 and 3). Although the fixation member 11 may be of various different constructions, in the embodiment illustrated, it includes a bearing in the form of an elongated cylindrical sleeve 17 having an outer end 19, an inner end 21, and an axial cylindrical passage 23 extending longitudinally through the sleeve. The sleeve 17, which may be considered as forming a peripheral wall around the passage 23, only partially circumscribes the passage at an outer end portion of the sleeve. More specifically, the sleeve 17 includes a semi-cylindrical section 25 adjacent its outer end 19. The inner end 21 of the sleeve 17 is annular.

The fixation member 11 includes means cooperable with a human eye 27 (FIG. 7) for fixing the fixation member to the eye. In the illustrated embodiment, such means includes four axially extending legs 29 equally spaced circumferentially and joined to the sleeve 17 by webs 31 which extend radially outwardly from the sleeve. The legs 29 lie radially outwardly of the sleeve 17 and terminate in teeth 33. Except for the teeth 33, the legs 29 terminate in essentially the same plane as the inner end 21.

Figure 4:
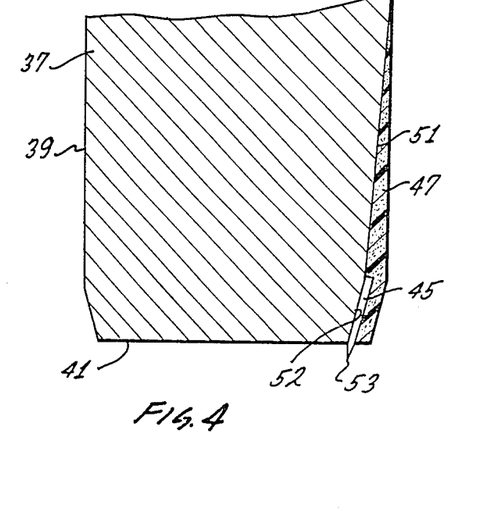
FIG. 4 is an enlarged, fragmentary sectional view taken generally along line 4—4 of FIG. 2.
Figure 4A:
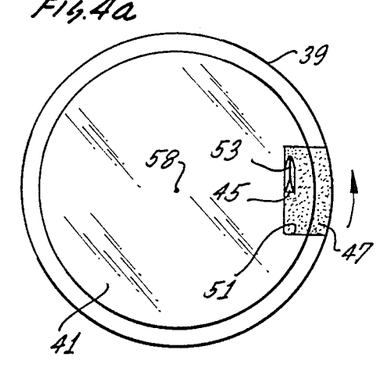
FIG. 4a is a bottom plan view of the knife of FIG. 2.
Figures 4B, 5B, 7:
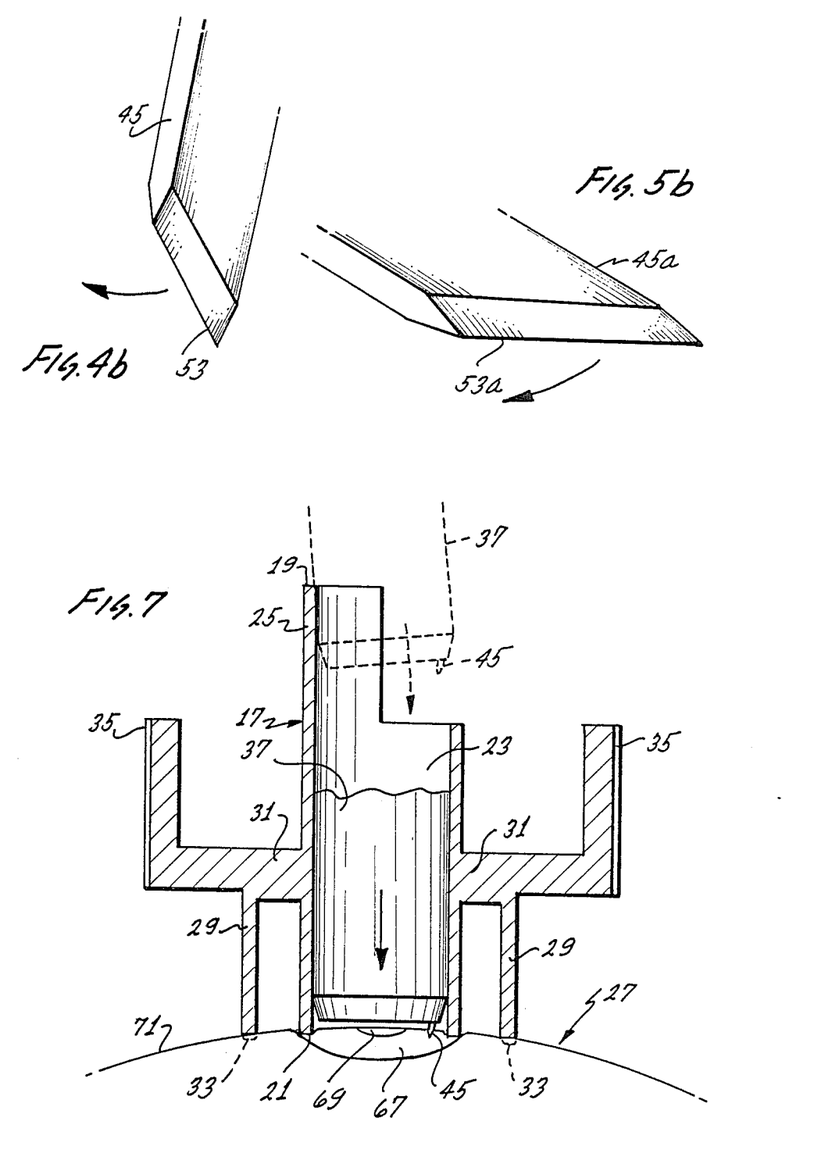
FIG. 4b is an isometric view of the blade used in the knife of FIG. 2.
FIG. 5b is an isometric view of the blade shown in FIG. 3.
FIG. 7 is a sectional view of the trephine affixed to the sclera, with the shaft as shown in dashed lines being inserted into the bearing and as shown in full lines almost fully axially advanced into the bearing.

To facilitate manually grasping the fixation member 11, two of the opposite legs 21 extend radially outwardly beyond the associated legs 29 and are joined to upwardly extending knurled tabs 35. As shown in FIGS. 1 and 7, the semi-cylindrical section 25 opens in the direction of one of the tabs 35 and extends axially beyond the tabs. In this embodiment, the fixation member 11 is integrally constructed of a suitable metal.

Although one or more of the knives can be provided, in this embodiment of the invention, the knives 13 and 15 are provided. The knives 13 and 15 are similar and, except to the extent shown or described herein, may be identical. Portions of the knife 15 corresponding to portions of the knife 13 are designated by corresponding reference numerals followed by the letter "a."

The knife 13 includes an elongated metal shaft 37 having a peripheral wall 39, an end wall 41 and a driving portion 43 for use in rotating the shaft, a blade 45, and a mounting body 47 for fixedly mounting the blade on the shaft. The shaft 37 has a conical portion 49 adjacent the end wall 41, and the peripheral wall 39 between the driving portion 43 and the conical portion 49 is essentially cylindrical. The driving portion 43 is radially thickened and is adjacent the end of the shaft 37 remote from the end wall 41. The shaft 37 has a shoulder 50 at the inner end of the driving portion 43.

The shaft 37 has a groove 51 (FIGS. 2, 4 and 4a) which opens at the end wall 41 and the peripheral wall 39 and which contains the mounting body 47. The groove 51 has an inclined inner wall 52 which is inclined radially inwardly as it extends axially toward the end wall 41, and a lower portion of the inner wall adjacent the end wall 41 is more sharply inclined radially inwardly. The mounting body 47 may be, for example, a suitable plastic which will fixedly bond the blade 45 to the shaft 37 in a predetermined orientation. The blade may lie along, and be supported by, the lower portion of the wall 52. The blade 45 is fixedly mounted in the sense that it cannot be moved with respect to the shaft 37 without deforming the blade.

The blade 45 is elongated and has a cutting edge 53 exposed beneath the end wall 41. Although the blade 45 can be of different constructions, in the embodiment illustrated, it is in the form of a straight linear member, and it is constructed of a diamond.

The extent to which the cutting edge 53 extends beyond the end wall 41, and the orientation of the blade 45 can be varied to accommodate particular cutting requirements. However, generally, the blade 45 will project only a short fixed distance beyond the end wall 41, and in the embodiment illustrated, a distance D1 (FIG. 6) from the cutting edge 53 to the end wall 41 is about 0.41 mm.

The angular orientation of the blade 45 may also be varied. However, if it is desired to use the blade 45 to obtain an essentially vertical cut in the cornea, it has been found necessary to incline at least the exposed portion of the blade radially inwardly. If this is not done, a vertical cut is not obtained in the cornea, and this is believed to be due to the unusual, non-rigid nature of the cornea. Although the angle of incline X1 (FIG. 6) can be selected depending upon the results desired, the angle of incline may be, for example, 15 degrees to 30 degrees. In the embodiment shown, the angle of incline X1 is 15 degrees. More specifically, the angle X1 is the acute angle formed by the axis 55 of the blade 45 and a reference line 57 which is parallel to the longitudinal axis 58 of the shaft 37. The cutting edge 53 is short, linear and extends generally tangentially to the direction of rotation as viewed in FIG. 4a.

Figure 5:
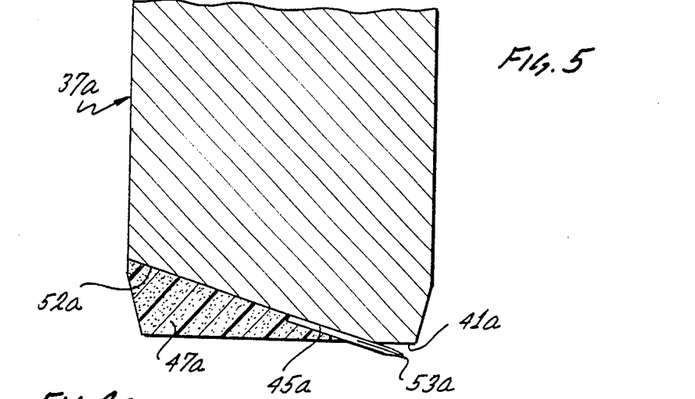
FIG. 5 is an enlarged, fragmentary sectional view taken generally along line 5—5 of FIG. 3.

Except for the presence of a pair (only one being shown in FIG. 3) of diametrically opposed, longitudinal grooves 59 in the peripheral wall 39a, a slight lengthening of the driving portion 43a and a different shape and orientation of the groove 51a, the shaft 37a may be identical to the shaft 37. The groove 51a preferably extends almost completely across the end wall 41a, and the groove has an inclined wall 52a as shown in FIG. 5. The mounting body 47a, like the mounting body 47, fills the groove in which it is positioned and has an appropriate contour to accomplish this objective.

Figure 5A:
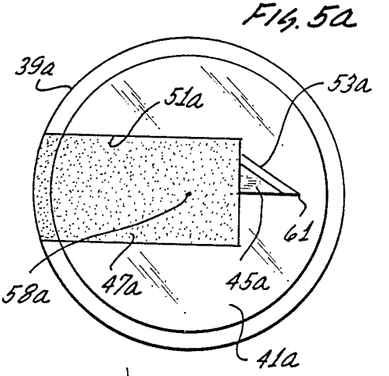
FIG. 5a is a bottom plan view of the knife of FIG. 3.

The blade 45a may lie along, and be supported by, the wall 52a as shown in FIG. 5 and project from the mounting body 47a and beyond the end wall 41a. The blade 45a terminates in an inclined cutting edge 53a as shown in FIG. 5a, and projects to a point 61. The blade 45a projects a fixed distance D2 beyond the end wall 41a. The distance D2 is less than the distance D1 and may be, for example, about 0.25 mm.

Figure 6:
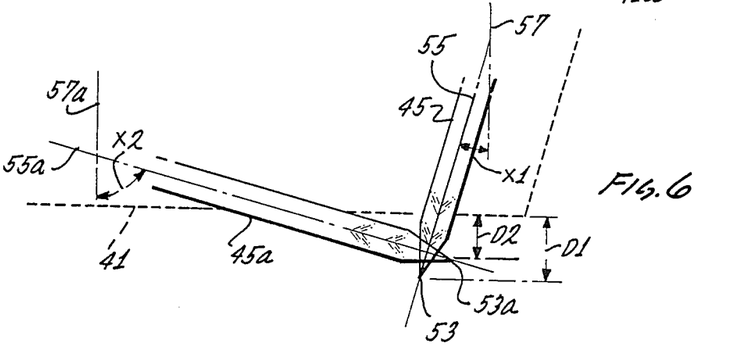
FIG. 6 is a schematic elevational view, with the blades of the two knives superimposed to show their relative orientations.

Although the blade 45a can extend at different angles, if it is to be used in combination with the blade 45 for groove-cutting purposes, it should be inclined radially outwardly at an angle X2 which, in this embodiment, is 75 degrees. More specifically, the angle X2 is defined by the axis 55a of the blade 45a and a reference line 57a which is parallel to the axis 58a of the shaft 37a. As shown in FIG. 6, with the blades 45 and 45a superimposed, the blades overlap such that the cutting edge 53 extends below the cutting edge 53a, and the cutting edge 53a extends radially outwardly beyond the cutting edge 53. As shown in FIG. 6, the blades 45 and 45a have different orientations with respect to the associated axes 58 and 58a.

To protect the blades 45 and 45a from damage, they both lie entirely within the perimeter of the associated peripheral wall 39 as viewed in a direction perpendicular to the associated end wall 41 and 41a. As shown in FIGS. 4a, 5a and 6, the cutting edges 53 and 53a lie adjacent the associated peripheral walls 39 and 39a.

To use the trephine of this embodiment of the invention, the fixation member 11 is placed over the eye 27 as shown in FIG. 7. Specifically, the inner end 21 of the sleeve 17 is brought into generally coaxial alignment with the cornea 67, and the pupil 69 and the teeth 33 are pushed slightly into the sclera 71 to fix the fixation member 11 to the eye 27 with the inner end 21 of the sleeve 17 engaging the cornea 67. During the placement of the fixation member 11, the fixation member can be manually grasped by the tabs 35 and retained in this fashion during the procedure.

Figure 8:
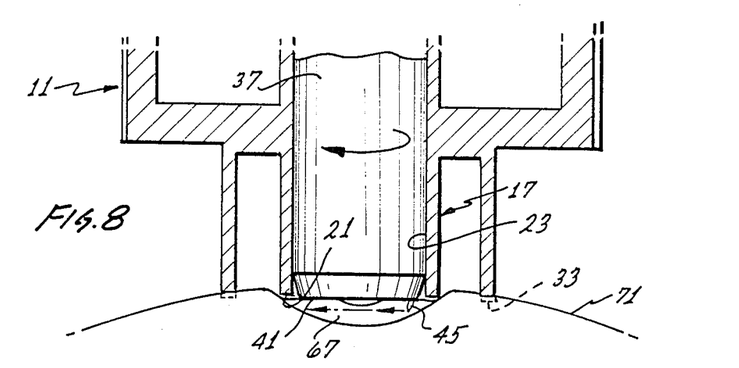
FIGS. 8-10 are views similar to FIG. 7 illustrating the steps in making successive cuts into the cornea using two different knives.
Figure 9:
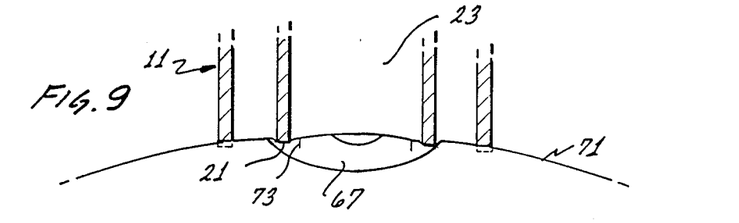

The shafts 37 and 37a are sized to be slidably and rotatably received within the passage 23 of the sleeve 17 as shown in FIG. 7 for rotation about a rotational axis which is essentially coincident with the axes 58 and 58a, respectively. More specifically, the shaft 37 is introduced into the passage 23 from the outer end 19 as shown in dashed lines in FIG. 7, with the blade 45 remote from the section 25 so as to avoid damaging the blade by contacting it against the outer end 19. The passage 23 slidably receives the shaft 37, and movement of the shaft 37 downwardly in the passage 23 can continue to an axial position (FIG. 8) in which the end wall 41 of the shaft 37 is out of the sleeve 17 and engages the cornea 67 with some slight force deemed appropriate by the surgeon, and the driving portion 43 is above the sleeve 17 so that it can be manually grasped to rotate the shaft. As shown in FIG. 8, forcing of the end wall 41 against the cornea tends to push the cornea away from the inner end 21 of the sleeve 17. In this axial position, the blade 45 enters the cornea 67 for a distance which is equal to, or directly related to, the fixed distance that the blade 45 projects beyond the end wall 41. Accordingly, manual rotation of the shaft 37 about the axis 58 for one revolution causes the blade 45 to make a first annular cut 73 (FIGS. 9 and 11) in the cornea 67. The cut 73 is essentially vertical.

Figure 10:
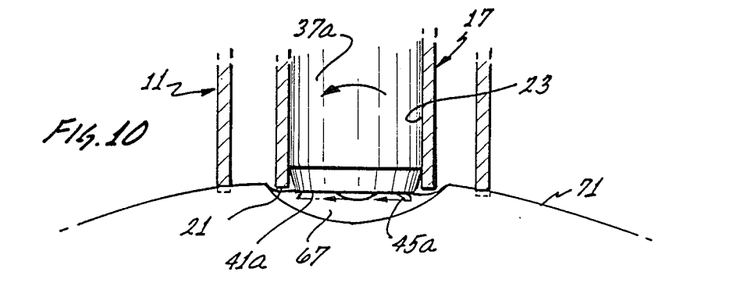
Figure 11:
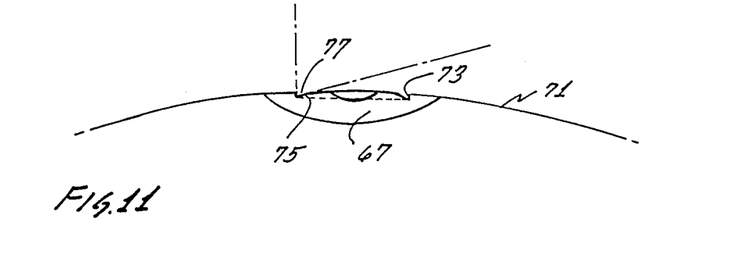
FIG. 11 is an elevational view of a portion of the eye showing the groove cut therein.

The shaft 37 is then withdrawn from the passage 23, and the shaft 37a is inserted into the passage to the axial position shown in FIG. 10 which may be identical to the axial position of the shaft 37 as described above. Thus, the end wall 41a is out of the sleeve 17 and engages the cornea 67 to push the cornea away from the inner end 21 and to cause the blade 45a to enter the cornea for a distance which is equal to, or directly related to, the fixed distance that the blade 45 projects beyond the end wall 41a. The shaft 37a is manually rotated within the sleeve 17 about the axis 58a for one revolution to form a second cut 75 in the cornea 67. The shaft 37a is then withdrawn from the passage 23, and the fixation member 11 is removed from the eye 27. The cuts 73 and 75 define an annular segment of the cornea which may be removed to define a groove 77 as shown in FIG. 11. The shoulders 50 and 50a are engageable with the outer end 19 to prevent the shafts 37 and 37a from being advanced too far into the passage 23.

Figures 12, 13, 14:
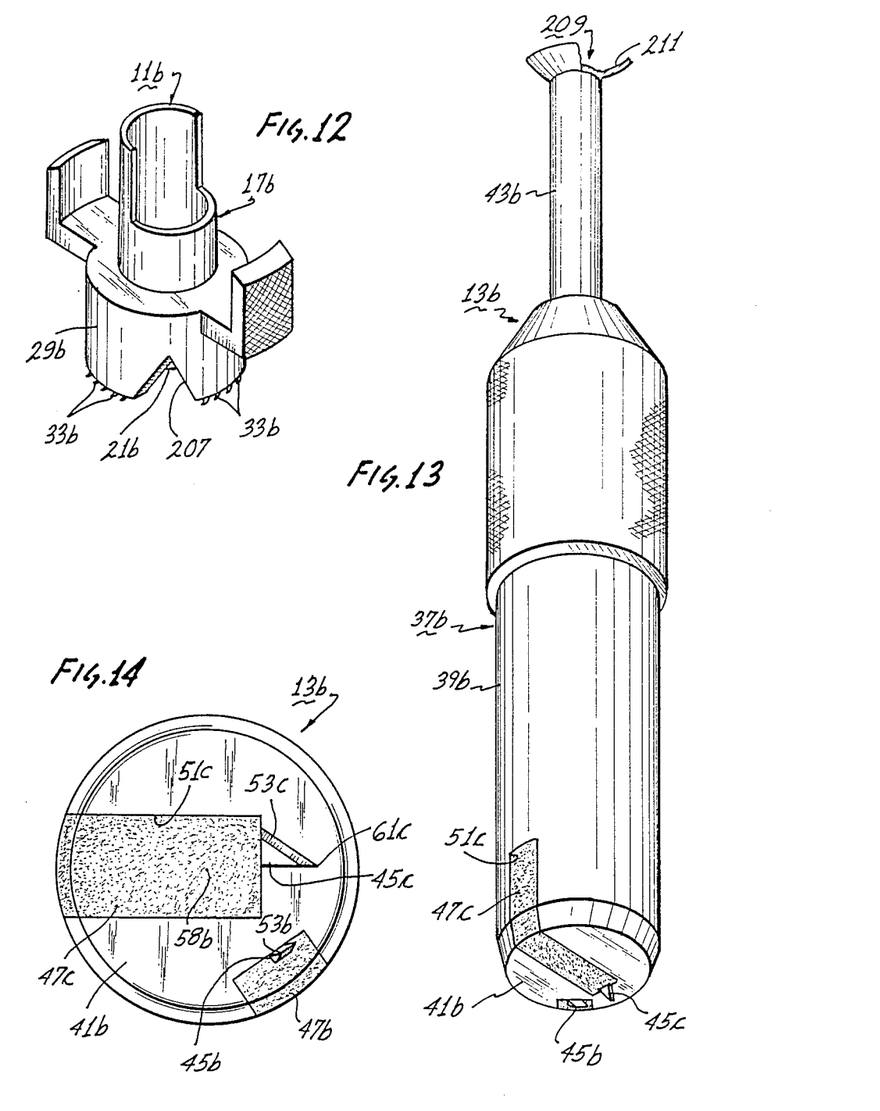
FIG. 12 shows a fixation member and FIG. 13 shows a knife.
FIG. 14 is a bottom plan view of the knife of FIG. 13.

FIGS. 12-16 illustrate a second embodiment of the trephine which includes a fixation member 11b and a single knife 13b (FIGS. 13 and 14). Portions of the fixation member 11b and portions of the knife 13b which correspond, respectively, to portions of the fixation member 11 and the knife 13 are designated by corresponding reference numerals followed by the letter "b." Portions of the knife 13b which correspond to selected portions of the knife 15 are identified by corresponding reference numerals followed by the letter "c." Except to the extent shown and described herein, the trephine of FIGS. 12-16 may be identical to the trephine of FIGS. 1-11.

One difference between the fixation member 11b and the fixation member 11 is that the inner end 21b of the sleeve 17b is elevated above the plane of the legs 29b. Stated differently, the legs 29b project axially beyond the inner end 21b in the direction of the teeth 33b to provide a space into which the cornea 67b (FIG. 15) can bulge.

Figure 16:
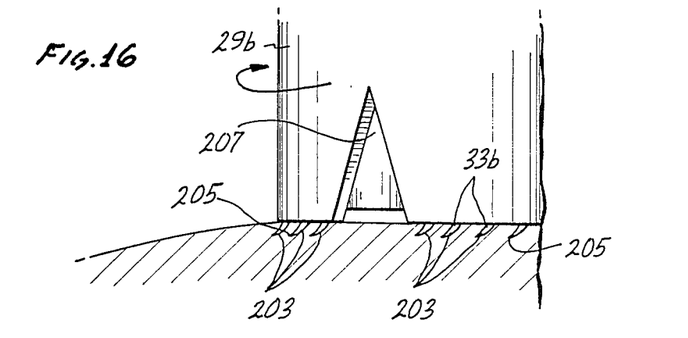
FIG. 16 is a fragmentary view showing an alternate construction for the teeth of the fixation member and adjacent portions of the eye.

Another difference between the fixation members 11 and 11b is that the fixation member 11b has teeth 33b (FIG. 16) terminating in a distal end portion 203 which extends in a direction having a component which extends circumferentially of the fixation member 11b. As explained more fully hereinbelow, this component which extends circumferentially also extends in the direction of rotation of the knife 13b within the fixation member 11b. Each of the teeth 33b terminates in a relatively sharp point 205 at its distal end. Some or all of the teeth 33b may be constructed as shown in FIG. 16. However, preferably a plurality of the teeth 33b are constructed to have their distal end portions having a component extending generally circumferentially of the fixation member 11b to assist in resisting rotation of the fixation member.

The fixation member 11b has relatively axially short notches 207 between the legs 29b. Accordingly, the legs 29b may be considered, if desired, as a single skirt-like leg having a plurality of the axially short notches 207 in its inner or lower edge. The fixation member 11b and any or all of the features embodied therein may be used with the knives 13 and 15 of the trephine of FIGS. 1-11 or with the single knife 13b.

The knife 13b terminates proximally in a driving portion 43b which is of less cross-sectional area than a major region of the shaft 37b located distally of the driving portion. More specifically, the driving portion 43b is generally cylindrical and is the smallest diameter portion of the shaft 37b. This facilitates rotation of the shaft 37b by the surgeon. The driving portion 43b terminates in an enlargement 209 which has a concave surface 211 opening away from the end wall 41b.

The primary difference between the knife 13b and the knives 13 and 15 of FIGS. 2 and 3 is that the knife 13b carries both of the blades 45b and 45c. With the blade 45c corresponding to the blade 45a of FIG. 3. The blades 45b and 45c may be mounted on the shaft 37b in the same manner as described above for the blades 45 and 45a, respectively. The blades 45b and 45c are arranged so that the cuts formed by them enable a segment to be severed from the cornea 67b to form a groove in the cornea. To best accomplish this, the blades are arranged so that the blade 45b follows or trails the blade 45c in the direction of rotation of the knife 13b. The cutting edges 53b and 53c are spaced circumferentially on the end wall 41b, and the angle between them can be varied as desired. In the illustrated embodiment, the angle between a central region of the cutting edge 53b and the adjacent edge of the blade 45c is about 45 degrees, but this is not critical. To enable the blades 45b and 45c to make the desired cuts in the cornea, the cutting edges are arranged to cut as the knife 13b is rotated about its axis 58b with the cuts formed thereby lengthening circumferentially as the shaft 37b is rotated. The blades 45b and 45c project from the end wall 41b of the shaft 37b in directions which are generally transverse to each other so that the desired groove can be cut. Finally, the blades 45b and 45c may be constructed of rubies, diamonds, synthetic or real sapphires, or any real or synthetic gem material or other suitable materials.

Figure 15:
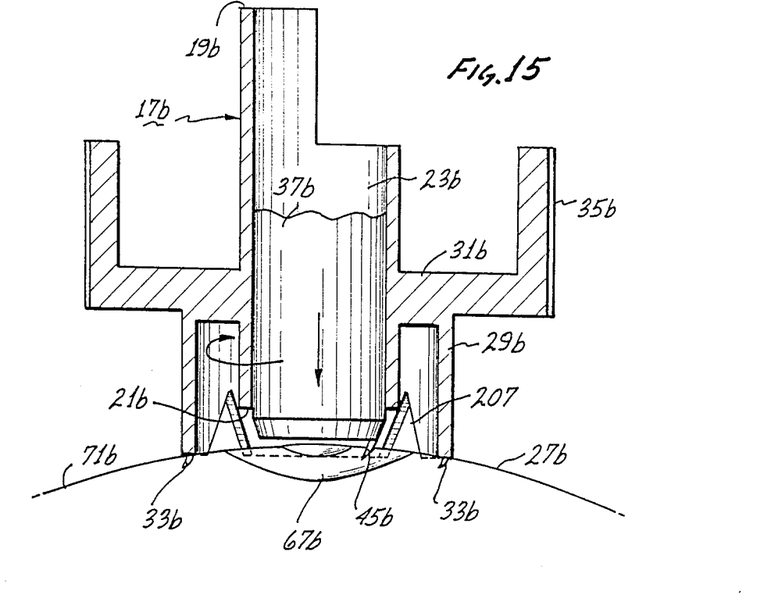
FIG. 15 is a sectional view of the trephine similar to FIG. 7 showing the trephine affixed to the sclera and with the shaft almost fully inserted into the bearing.

To use the trephine of this embodiment of the invention, the fixation member 11b is placed over the eye 27b as shown in FIG. 15 and as described above in connection with FIG. 7. The shaft 37b is introduced into the passage 23b from the outer end 19b as described in connection with FIG. 7 and rotated also as described above. The primary differences in the use of this embodiment of the trephine are in the rotation of the shaft 37b with the reduced diameter driving portion 43b and in the fact that the blades 45b and 45c operate simultaneously to form cuts which tend to form the groove in the cornea. Preferably, the manual rotation of the shaft 37b causes the blades 45b and 45c to cooperate to sever a complete annulus from the cornea 67b to thereby form the groove. However, some additional cutting action may be necessary to remove the annular section of the cornea 67b to form the groove.

The fixation member 11b is held between the thumb and middle finger of the surgeon's non-dominant hand with the index finger of that hand pushing downwardly on the enlargement 209 to apply the desired force to the knife 13b.

The rotation of the shaft 37b can be accomplished by rolling the driving portion 43b between the thumb and forefinger of the surgeon's dominant hand so that rotation of the surgeon's hands are not required. The driving portion 43b is of small enough diameter so that this rolling action preferably rotates the shaft 37b through slightly more than one revolution to remove, or partially remove, the annular segment from the cornea 67b.

As shown in FIG. 15, the inner end 21b is spaced from the cornea 67b. Accordingly, the inner end 21b does not engage and tend to flatten or distort the cornea. Also, because the inner end 21b is elevated above the cornea 67b, a space is provided into which the cornea can bulge.

Although exemplary embodiments of the invention have been shown and described, many changes, modifications and substitutions may be made by one having ordinary skill in the art without necessarily departing from the spirit and scope of this invention.

We claim:
1. A trephine for cutting a groove in the cornea of an eye, said trephine comprising:
 a fixation member including a bearing and means cooperable with the eye for fixing the fixation member to the eye;
 a shaft having an axis, a peripheral wall, an end wall, and a driving portion for use in rotating the shaft;
 first and second blades;
 means for mounting the first and second blades on the shaft with the blades projecting fixed distances beyond the end wall of the shaft;

said shaft being rotatable in said bearing relative to the fixation member with the end wall engaging the cornea; and said first blade having a first orientation with respect to the axis of the shaft and the second blade having a second orientation with respect to the axis of the shaft, said first and second orientations being arranged so that the cuts formed by the blades tend to enable a segment to be severed from the cornea to form the groove.

2. A trephine as defined in claim 1 wherein said first and second blades have first and second cutting edges, respectively, which are spaced circumferentially on the end wall.

3. A trephine as defined in claim 1 wherein said driving portion of said shaft terminates in an enlargement having a concave surface opening away from said end wall.

4. A trephine as defined in claim 1 wherein the driving portion of the shaft is of less cross-sectional area than a major region of the shaft located distally of the driving portion.

5. A trephine as defined in claim 1 wherein the bearing includes an elongated sleeve having a generally cylindrical passage which supports said shaft for rotation.

6. A trephine for cutting a groove in the cornea of an eye, said trephine comprising:
- a fixation member including a bearing and means cooperable with the eye for fixing the fixation member to the eye;
- a shaft having a peripheral wall, an end wall, an axis and a driving portion for use in rotating the shaft;
- first and second blades having first and second cutting edges, respectively;
- means for mounting the first and second blades on the shaft with the blades projecting fixed distances from the end wall of the shaft;
- said shaft being releasably receivable in said bearing for rotation relative to the fixation member with the end wall engaging the cornea; and
- said first cutting edge of said blade having a first orientation with respect to the axis of the shaft and the second cutting edge having a second orientation with respect to the axis of the shaft, said first and second cutting edges being arranged to form first and second cuts, respectively, in the cornea as the shaft is rotated in a first direction with said cuts lengthening circumferentially as the shaft is rotated and tending to form the groove in the cornea.

7. A trephine as defined in claim 6 wherein said cutting edges are spaced apart circumferentially.

8. A trephine as defined in claim 6 wherein the blades project from the end wall of the shaft in directions which are generally transverse to each other.

9. A trephine as defined in claim 8 wherein said cutting edges are spaced apart circumferentially.

10. A trephine as defined in claim 6 wherein said fixing means includes at least one leg coupled to the bearing and adapted to extend toward the sclera radially outwardly of the bearing, and a plurality of teeth projecting from said leg and engageable with the sclera, at least one of said teeth terminating in a distal end portion which extends generally in said first direction whereby said one tooth strongly resists rotation of the fixation member in said first direction.

11. A trephine as defined in claim 10 wherein said bearing has an inner end and said leg projects axially beyond said inner end in the direction of the cornea.

12. A trephine as defined in claim 6 wherein the driving portion of the shaft is of less cross-sectional area than a major region of the shaft located distally of the driving portion.

13. A trephine as defined in claim 12 wherein said fixing means includes at least one leg coupled to the bearing and adapted to extend toward the sclera radially outwardly of the bearing, and a plurality of teeth projecting from said leg and engageable with the sclera, at least one of said teeth terminating in a distal end portion which extends generally in said first direction whereby said one tooth strongly resists rotation of the fixation member in said first direction, said bearing has an inner end and said leg projects axially beyond said inner end in the direction of said teeth.

14. A trephine as defined in claim 6 wherein at least one of said cutting edges includes a ruby.

15. A trephine for making a cut in the cornea of an eye, said trephine comprising:
- a fixation member including a bearing and means cooperable with the eye for fixing the fixation member to the eye;
- a shaft having a peripheral wall, an end wall and a driving portion for use in rotating the shaft;
- a blade having a cutting edge;
- means for mounting the blade on the shaft with the cutting edge at least partially exposed;
- said shaft being rotatable in said bearing about a rotational axis to cause the blade to form a cut in the cornea when the blade is rotated in a first direction in the bearing; and
- said fixing means including at least one leg coupled to the bearing and adapted to extend toward the sclera radially outwardly of the bearing, and a plurality of teeth projecting from said leg and engageable with the sclera, at least one of said teeth terminating in a distal end portion which extends generally in said first direction whereby said one tooth strongly resists rotation of the fixation member in said first direction.

16. A trephine as defined in claim 15 wherein said bearing has an inner end and said leg projects axially beyond said inner end in the direction of said teeth.

17. A trephine as defined in claim 15 wherein said fixing means includes a plurality of said legs with each of said legs having at least one of said teeth thereon, at least some of said teeth terminating in a distal end portion which extends generally in said first direction whereby said some of said teeth strongly resist rotation of the fixation member in said one direction.

18. A trephine as defined in claim 15 wherein the driving portion of the shaft is of less cross-sectional area than a major region of the shaft located distally of the driving portion.

* * * * *